United States Patent [19]

Ueda

[11] Patent Number: 5,418,219
[45] Date of Patent: May 23, 1995

[54] PHARMACEUTICAL COMPOSITION FOR TREATMENT OF ADULT RESPIRATORY DISTRESS SYNDROME CONTAINING HUMAN ANP

[75] Inventor: Masakazu Ueda, Tokyo, Japan

[73] Assignee: Suntory Limited, Japan

[21] Appl. No.: 279,075

[22] Filed: Jul. 22, 1994

Related U.S. Application Data

[62] Division of Ser. No. 109, Jan. 4, 1993, abandoned.

[30] Foreign Application Priority Data

Jan. 1, 1992 [JP] Japan .................................. 4-002424

[51] Int. Cl.$^6$ ..................... A61K 38/02; A61K 38/12; A61K 38/16
[52] U.S. Cl. ........................................ 514/12; 514/11; 514/21
[58] Field of Search .............................. 514/12, 21, 11

[56] References Cited

U.S. PATENT DOCUMENTS

5,043,321  8/1991  Baertschi .............................. 514/12

FOREIGN PATENT DOCUMENTS

0147193  7/1985  European Pat. Off. .
0182984  6/1986  European Pat. Off. .

OTHER PUBLICATIONS

Chemical Abstracts, vol. 110, No. 17, 24 Apr. 1989 "Atrial natriuretic factor in chronic obstrutive lung disease with pulmonary hypertension" p. 518.
Biological Abstracts, vol. 84, No. 8, 1987 "Plasma Atrial natriuretic peptide and spontaneous diuresis in in sick neonates".
Biological Abstracts, vol. 90, No. 11, 1990 "Changes in plasma alpha human ANP concentrations during acute exacerbation of chronic respiratory failure".
Chemical Abstracts, vol. 106, No. 12, 23 Mar. 1987 "The role of alpha-atrial natriuretic peptide in fluid retention during mechanical ventalation with positive end-expiratory pressure" p. 359.
Biological Abstracts, vol. 94, No. 3, 1 Aug. 1992 "Atrial natriuretic peptide in the prediction of congestive heart failure rink in trial olderty" pp. 2625-2629.
Saito et al., Circulation 76(1), 115-124, 1987.

Primary Examiner—Howard E. Schain
Attorney, Agent, or Firm—Cushman Darby & Cushman

[57] ABSTRACT

The improved pharmaceutical composition for the treatment of adult respiratory distress syndrome (ARDS) contains a human atrial natriuretic peptide as an effective ingredient. It will combat ARDS against which no therapeutics have been found effective.

5 Claims, 5 Drawing Sheets

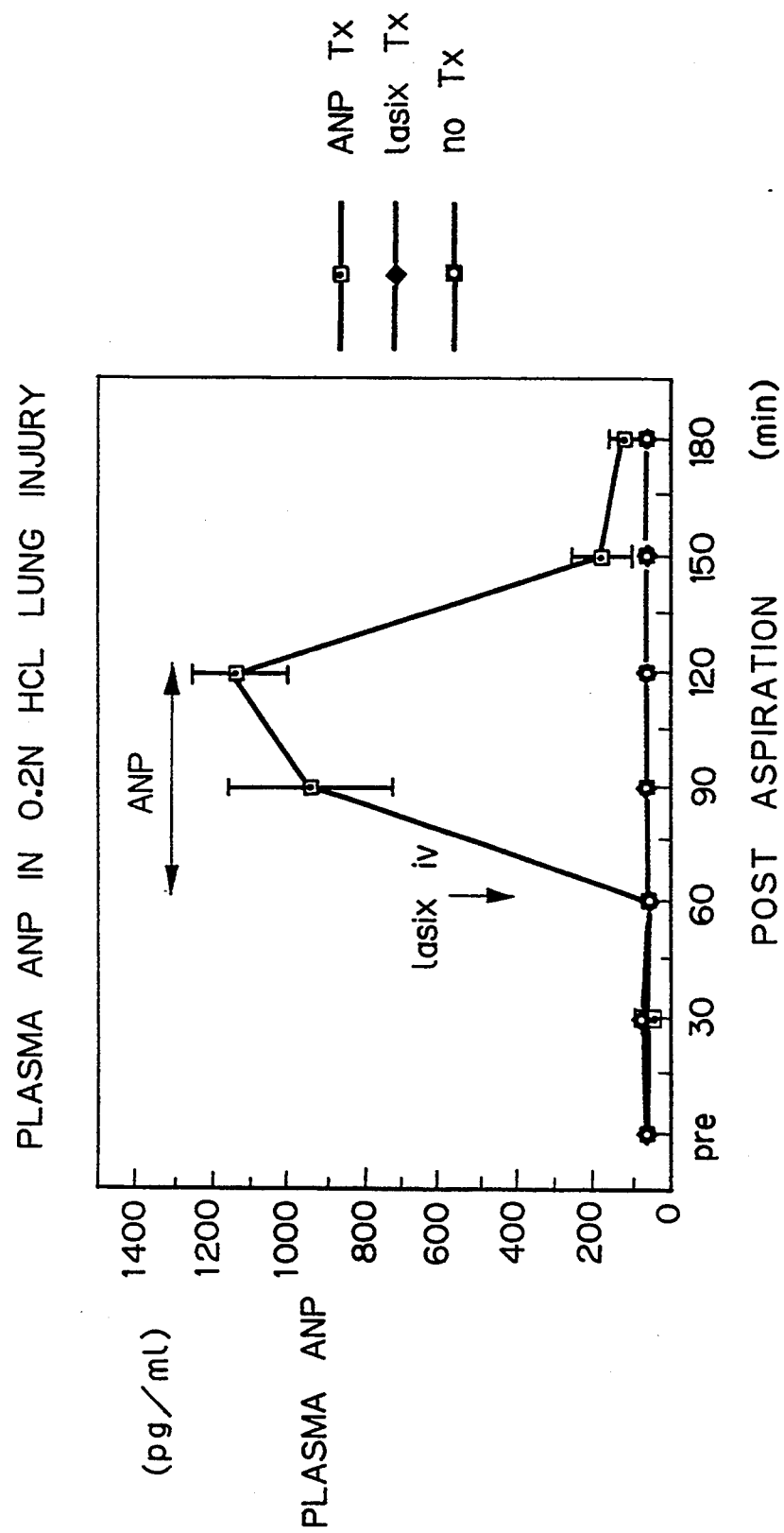

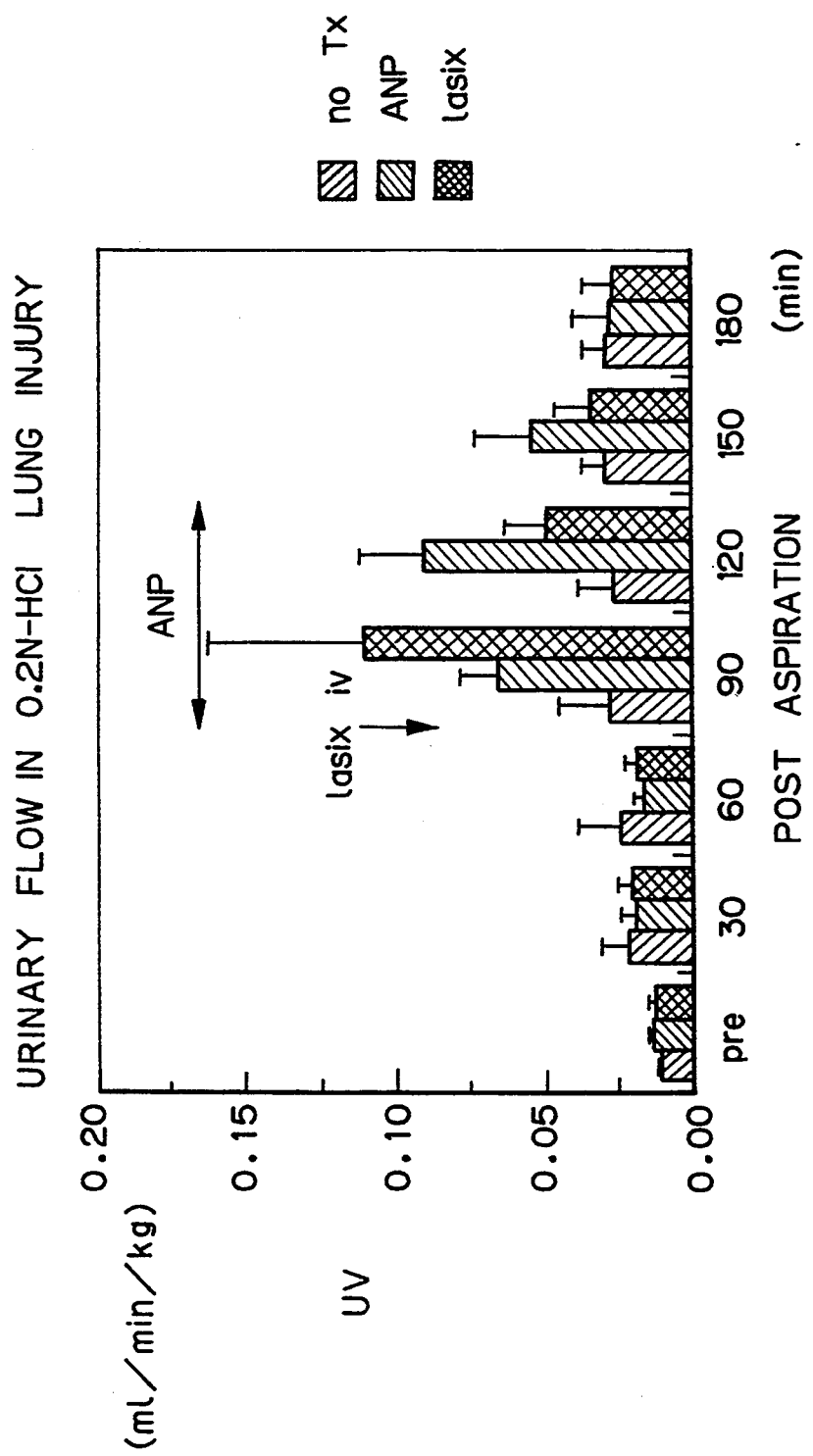

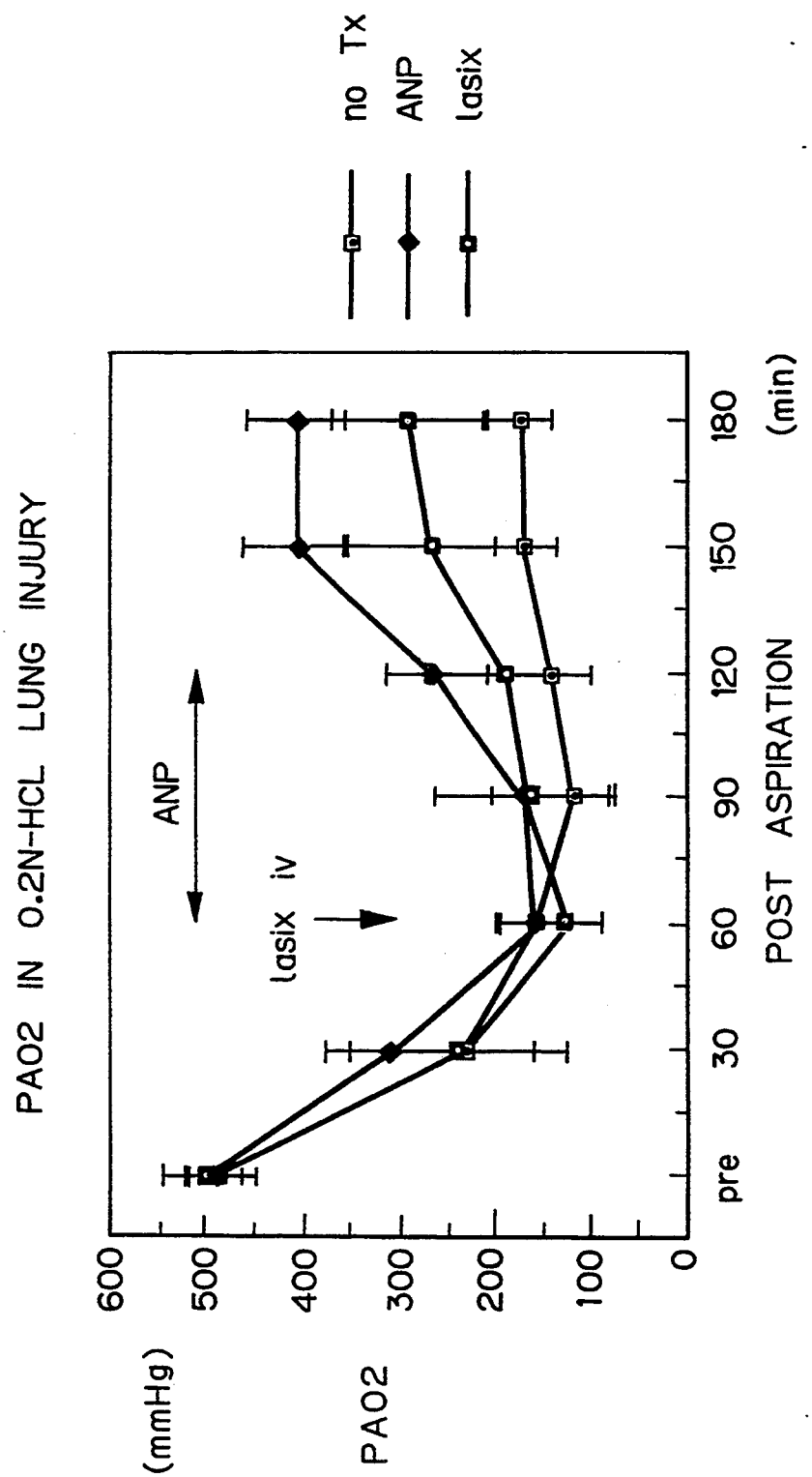

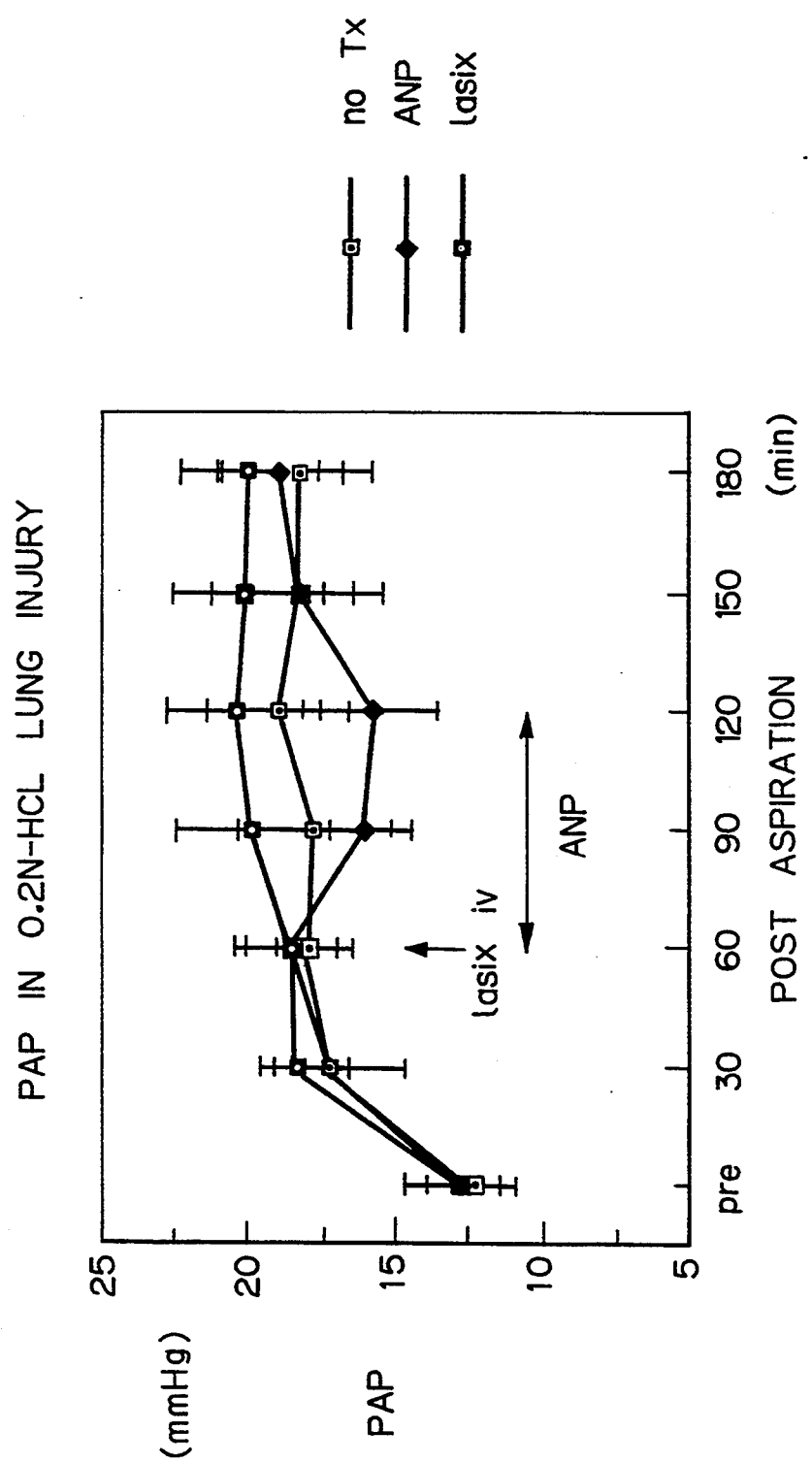

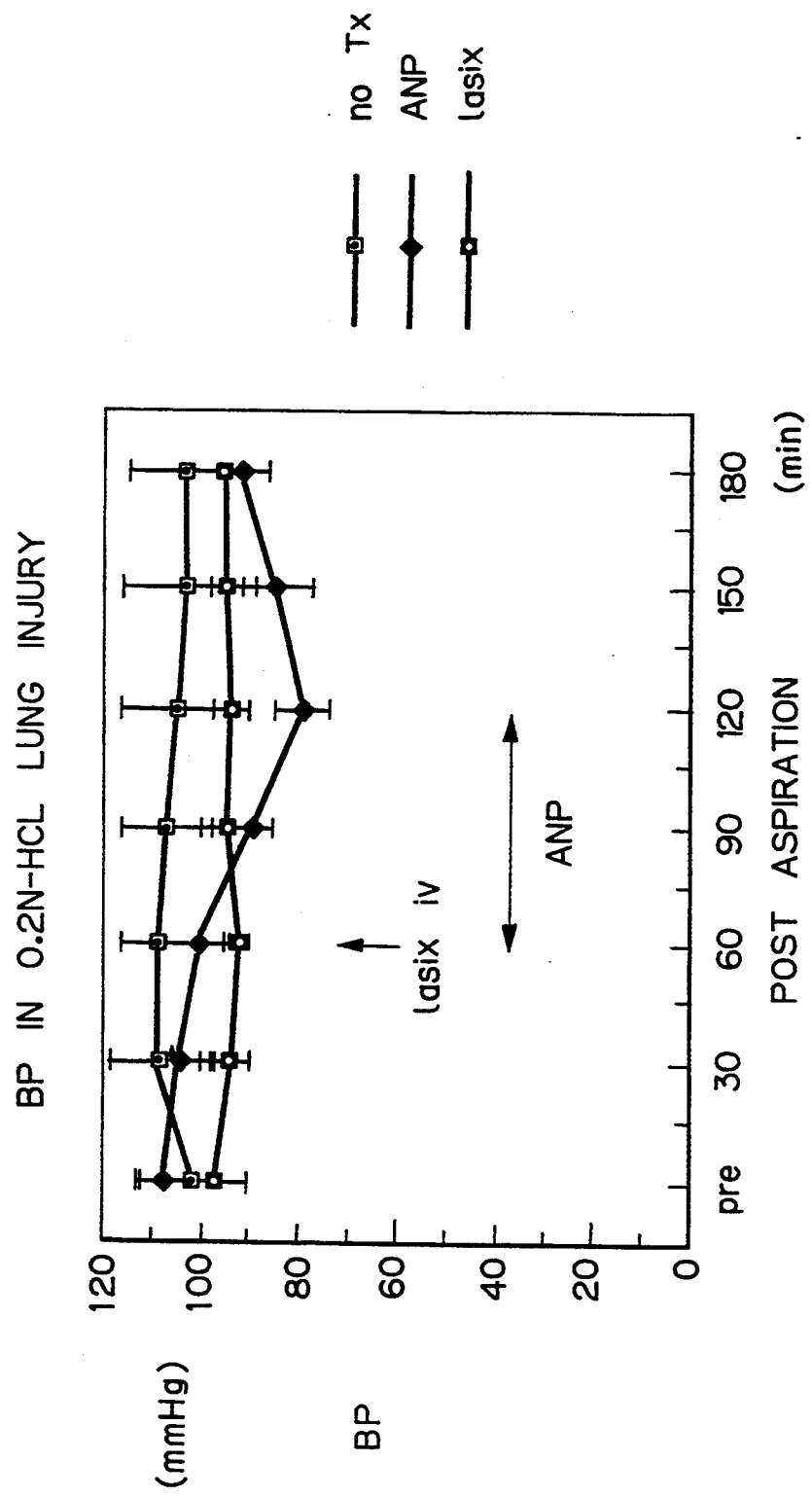

PHARMACEUTICAL COMPOSITION FOR TREATMENT OF ADULT RESPIRATORY DISTRESS SYNDROME CONTAINING HUMAN ANP

This is a division of application Ser. No. 08/000,109, filed on Jan. 4, 1993, which was abandoned upon the filing hereof.

BACKGROUND OF THE INVENTION:

This invention relates to a pharmaceutical composition for treatment of adult respiratory distress syndrome (ARDS) that contains a human atrial natriuretic peptide (hereunder abbreviated as "h-ANP") as an effective ingredient.

Adult respiratory distress syndrome (ARDS) is the general term for those manifestations of serious respiratory failure which occur in the trachea as a consequence of various predisposing conditions including shock, trauma, fracture, septicemia and drug intoxication. ARDS is characterized by interstitial edematous disorders resulting from enhanced permeability of the pulmonary vascular endothelium and the alveolar epithelium and causes such diseases as pulmonary edema and atelectasis and, in an extreme case, results in irreversible interstitial fibrosis and reduced pulmonary vascular beds. The first phase of ARDS is evidenced by the appearance of dyspnea, and the second phase by hypoxemia and infiltrations on chest X-ray. In the third phase, alveolar disorders proceed and the pulmonary compliance decreases so much as to render the institution of mechanical ventilation mandatory. The mortality rate up to this stage is about 50%; in the fourth phase, pulmonary fibrosis and infection become marked and the mortality rate is as high as about 80%.

One of the methods conventionally adopted to treat ARDS is respiratory management. This involves ventilation (positive end-expiratory pressure, which is hereunder abbreviated as "PEEP") in order to achieve improvements on the loss of pulmonary compliance and residual functional gas. In PEEP, an obstructed peripheral airway is cleared and collapsing alvedi are reinflated, thereby promoting gas exchange. However, as it has turned out, this approach causes two clinical problems, i.e., damage to tile alveolar epithelium and enhanced interstitial edema.

Speaking of drug therapy, there are no drugs available today that are effective against ARDS. Steroids such as prednisolone methyl acetate (Depo-medorole) have been administered in pulse in expectation of their ability to enhance vascular permeation or to suppress the release of proteases; however, those steroids have been shown to have no efficacy against ARDS.

Since it is known that many mediators released from neutrophils, macrophages and platelets take part in the development of ARDS, extensive review has been made of antagonists and synthesis inhibitors including peroxide scavengers such as SOD and vitamin E1, TXA2 synthesis inhibitors such as OKY-046, cycloxygenase inhibitors such as ibuprofen, and protease inhibitors such as urinastatin. However, the mechanism behind the development of ARDS cannot be explained by any single mediator, so none of the reagents studied for far have proved to be completely effective.

SUMMARY OF THE INVENTION

The present invention has been accomplished under these circumstances and has as an object providing a pharmaceutical composition effective against ARDS, more specifically, a pharmaceutical composition for treatment of ARDS that contains a human atrial natriuretic peptide as an effective ingredient.

BRIEF DESCRIPTION OF THE DRAWINGS:

FIG. 1 is a graph showing the time courses of plasma ANP levels in three groups of pigs as models with pulmonary injury, i.e., the first group being administered ANP, the second group administered furosemide (Lasix) and the third being control;

FIG. 2 is a graph showing the time courses of urinary volumes in three groups under the same conditions as used for constructing FIG. 1;

FIG. 3 is a graph showing the time courses of a partial pressure of oxygen in arterial blood of the animals as measured under the same conditions as used for constructing FIG. 1;

FIG. 4 is a graph showing the time courses of pulmonary arterial blood pressure of the animals as measured under the same conditions as used for constructing FIG. 1; and FIG. 5 is a graph showing the time courses of blood pressure of the animals as measured under the same conditions as used for constructing FIG. 1.

DETAILED DESCRIPTION OF THE INVENTION:

The ventilation by PEEP improves the gas exchange, while interstitial edema is observed and, at the same time, the plasma ANP level decreases. ANP is therefore anticipated to improve the edema.

The plasma ANP level of patients with ARDS is about 8 times as high as the level of healthy person.

From these facts, it is believed that ANP is produced and/or released in the patients to reduce the severity of pulmonary edema, thereby improving the process of gas exchange in patients with ARDS.

A typical example of the ANP that can be used in the present invention is an $\alpha$-hANP composed of 28 amino acid residues (see Japanese Patent Publication No. 19520/1988); it should, however, be noted that any peptides that have the ring structure and C terminus of the peptide at issue, namely, those which have amino acid residues in positions 7–28 of $\alpha$-hANP, can be used without limitations. The peptide at issue may be a naturally occurring one which is isolated and worked up to a pure state, or it may be produced by either chemical synthesis or gene recombinant technology.

The peptide to be used in the present invention may be in the form of a salt with a metal such as sodium, potassium, lithium or calcium, or with an organic base. Alternatively, the peptide may be in the form of a salt with a mineral acid such as sulfuric acid, hydrochloric acid or phosphoric acid, or with an organic acid such as acetic acid or maleic acid. Needless to say, the peptide of the present invention, if it is to be used as a pharmaceutical, may be in a free form or it may be a pharmaceutically acceptable salt.

The peptide of the present invention or a pharmacologically acceptable salt thereof is preferably mixed with a carrier, excipient, diluent or other pharmacologically acceptable vehicles that are known per se, then administered by the method commonly adopted for peptide-base pharmaceuticals, namely, by parenteral administration such as intravenous, intramuscular or subcutaneous administration. Oral administration is generally ineffective since the pharmaceutical composition of the present invention will undergo decomposition in the digestive tract; if desired, it may be administered perorally after being formulated in such a dosage form that it is less likely to be decomposed in the digestive tract, for example, as a microcapsule in which the peptide of interest (active ingredient) is confined in liposomes. Alternatively, the pharmaceutical composition may be administered in such a way that it will be absorbed through mucous membranes other than those in the digestive tract, as through the rectum, within the nose or under the tongue. In this case, the composition may be administered as a suppository, a nasal spray or as a sublingual tablet.

The dose of the pharmaceutical composition of the present invention varies with factors such as the diseases to be treated, the patient's age, his or her bodyweight, the severity of the disease and the route of administration; it can generally be administered in doses ranging from 0.1 μg/kg to 100 mg/kg, preferably from 0.5 μg/kg to 5 mg/kg, with the range of 1 μg/kg–1 mg/kg being more preferred.

1. Measurement on Assay model with Pigs

New Yorkshire male pigs weighing 16–24 kg were used in all experiments. The animals were allowed neither food nor water for 44 hr before test. They were initially anesthetized by intravenous injection of pentobarbital sodium (2.0 mg/kg) and pancuronium bromide (0.1 mg/kg) and, thereafter, the anesthetization was maintained by sustained intravenous injection of pentobarbital sodium (0.5 mg/kg/hr) and pancuronium bromide (0.1 mg/kg/hr). The animals were placed in prone position and ventilated at a frequency of 17 breaths/min with a tidal volume of 10–15 ml/kg, with the partial pressure of oxygen in arterial blood ($PaO_2$) being held at 35–45 Torr. Physiological saline (5 ml/kg) was initially infused by intravenous injection, followed by sustained intravenous injection for 30 min at a rate of 4 ml/kg/hr.

A Teflon catheter was inserted into the femoral artery of each animal for measuring blood pressure, blood ANP level and blood gas. At the same time, a pulmonary arterial cathether was inserted through the right cephalic vein for recording the changes in pulmonary arterial pressure. Pulmonary arterial pressure (PAP) and right atrial pressure (RAP) were measured with thermistor-tipped pressure transducers. Pulmonary capillary wedge pressure (PCWP) was measured with a baloon-fitted catheter. Cardiac output (CO) was calculated from the average of three measurements by the thermodilution method. Body temperature was measured with a thermistor inserted into the pulmonary artery and maintained at 37°–38° C. with the aid of a heat jacket. Electrocardiograms were induced from the four limbs and the ECC waveform and the number of heart beats were measured.

A cannula was inserted into the bladder of each animal and urine samples were collected at 30-min intervals. Blood sampling and hemodynamic measurements were also conducted at 30-min Intervals but intermediate between collections of urine samples. Blood samples for assaying blood α-hANP levels were collected into chilled glass tubes each containing EDTA (0.1 mg/ml) and aprotinin (500 KIU/ml). Sampled blood specimens were immediately centrifuged at 4° C. and plasma was stored frozen at −70° C. for no longer than two weeks prior to use in the measurement of α-hANP levels. Plasma α-hANP levels were measured by the RIA method using a rabbit anti α-hANP antibody.

2. Experimental Protocol

All specimens were allowed to equilibrate for 60 min until stable blood pressure, arterial blood gas and urinary excretion were attained. The first 30-min values following the time when the three parameters became stable were used as baseline data. With the aid of a polyethylene catheter inserted into the trachea, 0.1 N HCl (2.0 ml/kg) was instilled into lungs on both sides over 30 sec, thereby inducing pulmonary injury. Tests were performed on the following three groups of animals, each consisting of five heads.

(1) Group I: ANP group (pigs in which lung injury was induced were administered ANP); α-hANP dissolved in 0.025 ml of 0.5% BSA was administered by sustained intravenous injection at a rate of 0.1 μg/kg/min through the right external Jugular vein for a period of 6 hr (from 60 to 120 min after HCl aspiration).

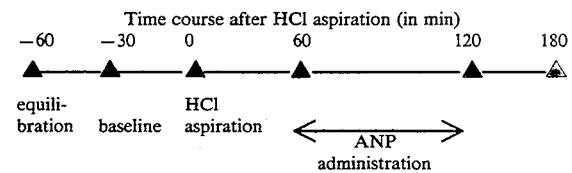

(2) Group II: Furosemide group (pigs in which lung injury was induced were administered furosemide (Lasix of Hoechst AG); 60 min after HCl aspiration, furosemide (0.05 mg/kg) was administered by rapid intravenous Injection; thereafter, 0.5% BSA was administered by sustained intravenous injection at a rate of 0.025 ml/kg/min for a 6-hr period from 60 to 120 min after HCl aspiration.

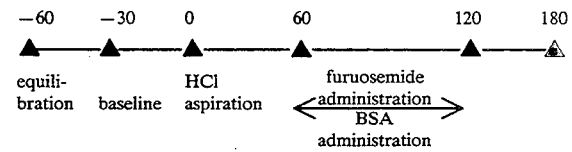

(3) Group III: Control group (pigs in which pulmonary injury was induced were administered BSA); 0.5% BSA was administered by sustained injection at a rate of 0.025 ml/kg/min for a 6-hr period from 60 to 120 min after HCl aspiration.

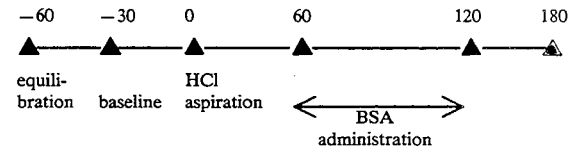

The following examples are provided for the purpose of further illustrating the present invention but are in no way to be limiting.

EXAMPLE 1: PLASMA ANP LEVEL

The plasma ANP level of the ANP group was 47.9 ±10.5 pg/ml at 60 min after HCl aspiration (just before ANP administration) but, after 60-min sustained intravenous injection of ANP (120 min after HCl aspiration), the plasma ANP level rose to 1130.6 ±123.19 pg/ml. It decreased sharply to 118.5 ±38.95 pg/ml 60 min after the end of ANP administration (180 min after HCl aspiration).

On the other hand, no marked changes in plasma ANP level occurred in the control group or furosemide (Lasix) group.

The results of Example 1 are shown in FIG. 1.

EXAMPLE 2: URINE EXCRETION

In the ANP group, the rate of urine excretion was 0.016 ±0.03 ml/kg/min at 30–60 min after HCl aspiration; however, for the first 30 min of ANP administration (60–90 min after HCl aspiration), the rate of urine excretion rose to 0.065±0.013 ml/kg/min. The rate returned to 0.028±0.11 ml/kg/min, 30–60 min after the end of ANP administration (150–180 min after HCl aspiration).

In the furosemide group, the rate of urine excretion was 0.018±0.004 ml/kg/min at 30–60 min after HCl aspiration; however, for the first 30 min of furosemide administration (60–90 min after HCl aspiration), the rate of urine excretion rose to 0.110±0.052 ml/kg/min, returning to 0.027±0.009 ml/kg/min at 30–60 min after the end of furosemide administration (150–180 min after HCl aspiration). The total amount of urine collected from the ANP group after ANP administration (60–180 min after HCl aspiration) was 0.251±0.061 ml/kg/120 min whereas the value for the furosemide group was 0.205±0.068 ml/kg/120 min; obviously, there was no significant difference between the two values.

In the control group, the rate of urine excretion rose from the baseline 0.010±0.002 mg/kg/min (before HCl aspiration) to 0.028±0.008 ml/kg/min at 120–150 min after HCl aspiration. However, the total amount of urine collected from the control group for the period 60–180 min after HCl aspiration was 0.110±0.045 ml/kg/120 min, significantly smaller than the values for the ANP and furosemide groups ($p<0.05$).

The results of Example 2 are shown in FIG. 2. ANP and furosemide were comparable to each other in the intensity of their diuretic action.

EXAMPLE 3: PARTIAL PRESSURE OF OXYGEN IN ARTERIAL BLOOD ($PaO_2$)

The value of $PaO_2$ at 60 min after HCl aspiration was lower than the baseline value (before HCl aspiration) in each of the control, ANP and furosemide groups. However, there were no significant differences between the three groups in terms of $PaO_2$ values before and 60 min after HCl aspiration as discussed below in detail.

In the ANP group, $PaO_2$ decreased from the baseline 495.7±20.1 mmHg to 153.86±37.94 mmHg at 60 min after HCl aspiration. At 60 min after ANP administration (180 min after HCl aspiration), $PaO_2$ returned to 404.5±48.2 mmHg, which was the highest of the three groups ($p<0.05$ against the furosemide group and $p<0.001$ against the control group). In the furosemide group, $PaO_2$ which was 490.3±29.0 mmHg at the baseline decreased to 120.5±33.1 mmHg at 60 min after HCl aspiration. At 60 min after furosemide administration (180 min after HCl aspiration), $PaO_2$ increased to 287.9±78.2 mmHg ($p<0.05$ against the control group). In the control group, $PaO_2$ decreased from the baseline 495.7±48.6 mmHg to 152±43.2 mmHg at 60 min after HCl aspiration. The $PaO_2$ value at 180 min after HCl aspiration was 171.1 35 32.6 mmHg and had no significant difference from the value at 60 min.

The results of Example 3 are shown in FIG. 3. The decrease in $PaO_2$ which was induced by HCl aspiration could be compensated by ANP and furosemide but ANP was more effective than furosemide.

EXAMPLE 4: PULMONARY ARTERIAL PRESSURE (PAP)

It has been reported that ANP has a basodilating action and, hence, ANP is anticipated to have a capability for lowering PAP. In addition, lowering PAP is important for effective treatment of acute pulmonary injury due to ARDS.

In the ANP group, PAP which was 12.7±1.3 mmHg at the baseline increased to 18.5±1.6 mmHg at 60 min after HCl aspiration ($p<0.01$ against the baseline value; no significant difference between the control and furosemide groups for the 60-min PAP after HCl aspiration). After 60 min of ANP administration (120 min after HCl aspiration), PAP decreased to 15.6±2.0 mmHg ($p<0.01$ against the baseline value, and $p<0.05$ against the control and furosemide groups for the passage of 120 min after HCl aspiration); at 60 min after the end of ANP administration (180 min after HCl aspiration), PAP returned to 18.9±2.1 mmHg (no significant difference between the furosemide and control groups for the 180-min PAP after HCl aspiration).

In the furosemide group, PAP increased from the baseline 12.7±1.9 mmHg to 20.4±2.3 mmHg after 60 min of furosemide administration (120 min after HCl aspiration).

In the control group, PAP which was 12.2±0.8 mmHg at the baseline increased to 18.9±2.4 mmHg at 120 min after HCl aspiration.

The results of Example 4 are shown In FIG. 4. ANP could lower PAP levels but furosemide was not shown to have the PAP lowering action.

EXAMPLE 5: BLOOD PRESSURE (BP)

In the ANP group, BP which was 100.8±8.8 mmHg at the baseline decreased to 79.4±4.7 mmHg after 60 min of ANP administration (120 min after HCl aspiration). At 60 min after the end of ANP administration (180 min after HCl aspiration), BP returned to 91.8±5.6 mmHg (no significant difference between the furosemide and control groups).

No significant changes in BP were observed in the furosemide group or the control group.

The results of Example 5 are shown in FIG. 5. ANP could lower BP levels but furosemide was not shown to have the BP lowering action.

It has been demonstrated that ANP is effective for the treatment of ARDS in animal models. Therefore, one may well anticipate that ANP will work effectively as a fluid regulating factor in patients with ARDS to alleviate respiratory failure. ARDS is a disease that requires treatment in ICUs but there are no drugs available today that are effective against ARDS; hence, in view of the great need of clinicians for an effective drug against ARDS, the pharmaceutical composition of the present invention for the treatment of ARDS has great benefits to the medical field.

What is claimed is:

1. A method for treating adult respiratory distress syndrome (ARDS) which comprises administering a patient in need of such treatment an effective amount of human atrial natriuretic peptide (h-ANP).

2. A method according to claim 1, wherein said effective amount of h-ANP ranges from 0.1 μg/kg to 100 mg/kg of the patient's body weight.

3. A method according to claim 2 wherein said effective amount ranges from 0.5 μg/kg to 5 mg/kg.

4. A method according to claim 1 wherein h-ANP is parenterally administered to the patient.

5. A method according to claim 1 wherein h-ANP is administered to the patient in such a way that it is absorbed through mucous membranes other than those of the digestive tract.

* * * * *

UNITED STATES PATENT AND TRADEMARK OFFICE
CERTIFICATE OF CORRECTION

PATENT NO. : 5,418,219

DATED : May 23, 1995

INVENTOR(S) : Masakazu UEDA

It is certified that error appears in the above-identified patent and that said Letters Patent is hereby corrected as shown below:

On the title page, item:

[30] Foreign Application Priority Data: Change "Jan. 1, 1992" to --Jan. 9, 1992--.

Signed and Sealed this

Seventh Day of November, 1995

Attest:

BRUCE LEHMAN

Attesting Officer

Commissioner of Patents and Trademarks